(12) United States Patent
Ouchi

(10) Patent No.: US 6,547,723 B1
(45) Date of Patent: Apr. 15, 2003

(54) FULLY-SWALLOWABLE ENDOSCOPIC SYSTEM

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 53 days.

(21) Appl. No.: 09/588,306

(22) Filed: Jun. 6, 2000

(30) Foreign Application Priority Data

Jun. 7, 1999 (JP) .......................................... 11-160032

(51) Int. Cl.[7] .............................................. A61B 1/005
(52) U.S. Cl. ...................... 600/146; 600/130; 600/139; 600/152
(58) Field of Search ................................ 600/101, 109, 600/128, 130, 136, 139, 146, 143, 151, 152, 141; 348/65, 68, 71, 74

(56) References Cited

U.S. PATENT DOCUMENTS

| | | | |
|---|---|---|---|
| 5,398,670 A | * 3/1995 | Ortiz et al. | 600/109 |
| 5,595,565 A | * 1/1997 | Treat et al. | 600/101 |
| 5,604,531 A | * 2/1997 | Iddan et al. | 600/109 |
| 5,662,587 A | * 9/1997 | Grundfest et al. | 600/114 |
| 6,162,171 A | * 12/2000 | Ng et al. | 600/101 |
| 6,240,312 B1 | * 5/2001 | Alfano et al. | 600/476 |

FOREIGN PATENT DOCUMENTS

| | | | |
|---|---|---|---|
| GB | WO 98/11816 | * | 3/1998 |
| JP | 64-4450 | | 1/1989 |
| JP | 64-76822 | | 3/1989 |
| JP | 3-9705 | | 1/1991 |
| JP | 4-144533 | | 5/1992 |
| JP | 6-114064 | | 4/1994 |
| JP | 7-111985 | | 5/1995 |

* cited by examiner

Primary Examiner—John P. Leubecker
(74) Attorney, Agent, or Firm—Greenblum & Bernstein, P.L.C.

(57) ABSTRACT

A fully-swallowable endoscopic system includes a rod-shaped endoscope body which can be swallowed entirely by a patient to be examined so as to be placed in a body cavity, the rod-shaped endoscope body including at least one bendable portion which is bendable along a curve of the body cavity; and an external device provided separately from the rod-shaped endoscope body having no mechanical connection with the rod-shaped endoscope body. The rod-shaped endoscope body is provided therein with at least two light emitters; at least two observing systems; a transmitter for transmitting a radio wave which carries an image formed by the observing system; and a power supplying device. The external device includes a receiver for receiving the radio wave which carries the image.

22 Claims, 16 Drawing Sheets

FULLY-SWALLOWABLE ENDOSCOPIC SYSTEM

BACKGROUND OF THE INVENTION

1. Field of the Invention

The present invention relates to a fully-swallowable endoscopic system which can be retained in the patient's body for a long time, wherein few blind spots occur in an endoscopy examination.

2. Description of the Related Art

In an endoscopy examination, in general, an insertion portion connected to an operation portion is introduced into a patient's body through his or her mouth to observe a target inner part of the body. In a typical front-view endoscope for viewing from the front of the tip of the insertion portion, or a typical side-view endoscope for viewing from the side of the insertion portion, a target inner part of the body can be viewed from only a single direction. Due to this structure, in the case of observing an inner part of a largely-bent tubular passage in a body such as part of the large intestine, the occurrence of blind spots in the endoscopy examination cannot be avoided.

The body insertion portion of the endoscope must be sometimes inserted and retained in the body for a long time to observe the progress of a diseased part within the body or obtain and/or record somatoscopic information of a patient under ordinary every-day living conditions. However, the insertion and retainment of the endoscope in the body through the patient's mouth causes the patient to suffer from significant pain.

To relieve pain from the patient, it is known to use a capsule type endoscope which is provided at an intermediate portion of a flexible continuous member, as disclosed in Japanese Unexamined Patent Publication No. 64-76822. A patient to be examined swallows a soft ball formed at a tip end of the flexible continuous member the night before the day of examination, so that the soft ball is discharged from the patient's anus the next day. An operator pulls or moves the tip end and the tail end of the flexible continuous member to thereby move or guide the capsule connected to the intermediate portion of the flexible continuous member.

In the capsule type of endoscope described above, the pain that the patient suffers can be eased in comparison with conventional endoscopes. However, the patient must always carry the flexible continuous member whose one end extends out of his or her mouth for more than 12 hours. Consequently, it is impossible for the patient to take a meal or speak. Under these circumstances, no substantial pain relieving effect can be expected. Moreover, it is generally difficult to control the position of the endoscope when in the form of a capsule.

SUMMARY OF THE INVENTION

It is an object of the present invention to provide a fully-swallowable endoscopic system which can relieve a patient to be examined from pain and which makes it possible to observe the target inner part of the body surely and precisely.

To achieve the object mentioned above, according to the present invention, a fully-swallowable endoscopic system is provided, which includes a rod-shaped endoscope body which can be swallowed entirely by a patient to be examined so as to be placed in a body cavity, the rod-shaped endoscope body including at least one bendable portion which is bendable along a curve of the body cavity; and an external device provided separately from the rod-shaped endoscope body having no mechanical connection with the rod-shaped endoscope body. The rod-shaped endoscope body is provided therein with at least two light emitters, at least two observing systems, a transmitter for transmitting a radio wave which carries an image formed by the observing system; and a power supplying device. The external device includes a receiver for receiving the radio wave which carries the image.

Preferably, one of the at least two light emitters and one of the at least two observing systems are provided in one of the opposite ends of the rod-shaped endoscope body, and another one of the at least two light emitters and another one of the at least two observing systems are positioned in the other of the opposite ends of the rod-shaped endoscope body.

Each of the one and the another of the at least two observing systems can be a front-view observing system for viewing from the front of a corresponding one of the opposite ends of the rod-shaped endoscope body.

In an embodiment, one of the at least two observing systems is a front-view observing system for viewing from the front of a corresponding one of the opposite ends of the rod-shaped endoscope body; and the another one of the at least two observing systems is a side-view observing system for viewing from the side of the rod-shaped endoscope body.

Preferably, the rod-shaped endoscope body includes at least one flexible portion which is constituted from at least one bendable portion and which bends when an external force is applied to the at least one flexible portion. Each of the at least one bendable portion is provided therein with a bending portion which can be radio-controlled to bend by an operation of the external device. The rod-shaped endoscope body is provided therein with a radio-controlled driving device which receives a radio operational signal transmitted from the external device to bend the bending portion in accordance with the radio operational signal. The external device includes an operational portion which is operated to transmit the radio operational signal to the radio-controlled driving device.

In an embodiment, the at least one bendable portion includes a plurality of bendable portions arranged at different positions in the longitudinal direction of the rod-shaped endoscope body.

In an embodiment, the radio-controlled driving device includes a plurality of drive wires made of a shape memory alloy, and a selective-heating device which selectively heats the plurality of drive wires to bend the bending portion.

The power supplying device can be a built-in battery.

Preferably, the external device includes a microwave transmitter for transmitting a microwave to the rod-shaped endoscope body. The power supplying device converts the microwave into electrical current to supply the electrical current to the rod-shaped endoscope body.

Preferably, each of the at least two observing systems includes an objective optical system and a CCD image sensor.

Preferably, the external device includes a monitor which visually indicates the image.

According to another aspect of the present invention, a fully-swallowable endoscopic system is provided, which includes a rod-shaped endoscope body having at least one bending portion, at least one flexible portion connected to the at least one bending portion, at least two light emitters, corresponding at least two image pick-up devices, each taking an image of a target inner part illuminated by a corresponding one of the at least two light emitters, and a transmitter for transmitting a radio wave which carries the image taken by each of the at least two image pick-up devices; and a radio controller for manipulating the at least one bending portion to bend by radio-control.

Preferably, the rod-shaped endoscope body further includes a first hard portion fixed to one of the opposite ends of the rod-shaped endoscope body, wherein one of the at least two light emitters and one of the at least two image pick-up devices are fixed to the first hard portion.

Preferably, the rod-shaped endoscope body further includes a second hard portion fixed to the other of the opposite ends of the rod-shaped endoscope body, wherein the another one of the at least two light emitters and another one of the at least two image pick-up devices are fixed to the second hard portion.

Preferably, the radio controller includes a monitor and a receiver for receiving the radio wave to indicate the image on the monitor.

Preferably, the radio controller further includes a second transmitter for transmitting a microwave to the rod-shaped endoscope body, and wherein the rod-shaped endoscope body is provided therein with a power supplying device which receives the microwave to convert the microwave into electrical current which is to be used as a power source of the rod-shaped endoscope body.

The present disclosure relates to subject matter contained in Japanese Patent Application No.11-160032 (filed on Jun. 7, 1999) which is expressly incorporated herein by reference in its entirety.

BRIEF DESCRIPTION OF THE DRAWINGS

The invention will be discussed below in detail with reference to the drawings, in which.

DESCRIPTION OF THE PREFERRED EMBODIMENTS

Figure 1:
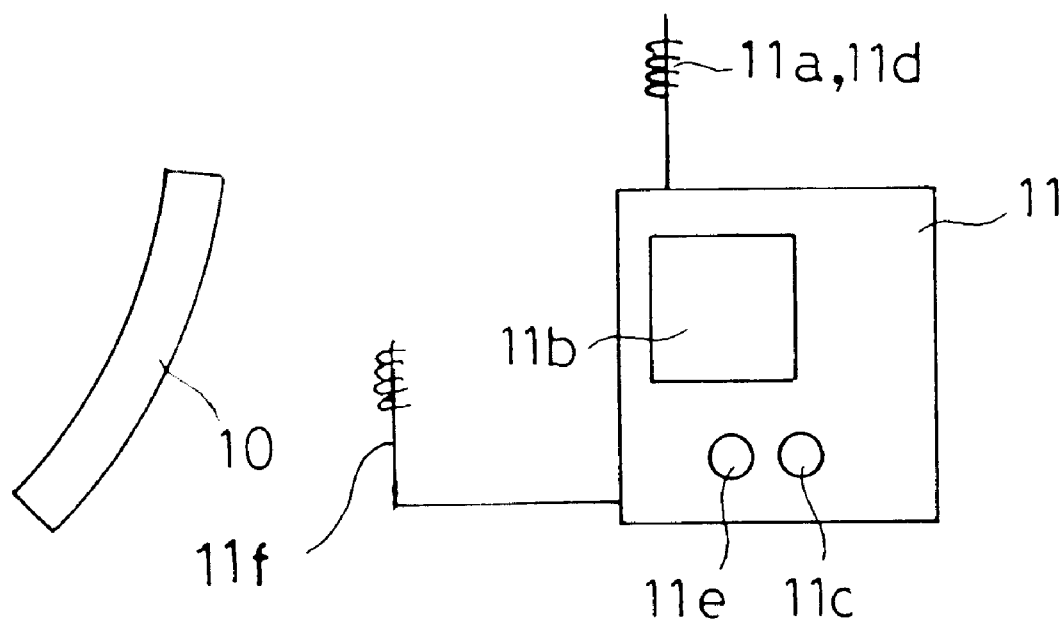
FIG. 1 is a schematic view of an embodiment of a fully-swallowable endoscopic system comprising a rod-shaped endoscope body and an external device, according to the present invention.

FIG. 1 shows an embodiment of a fully-swallowable endoscopic system which includes a rod-shaped endoscope body 10 and an external device 11. A patient to be examined swallows the rod-shaped endoscope body 10 before an endoscopic examination is performed with the endoscope 10. The external device 11 functions as a wireless controller (radio controller) and a power supply for the endoscope 10.

Figure 2:
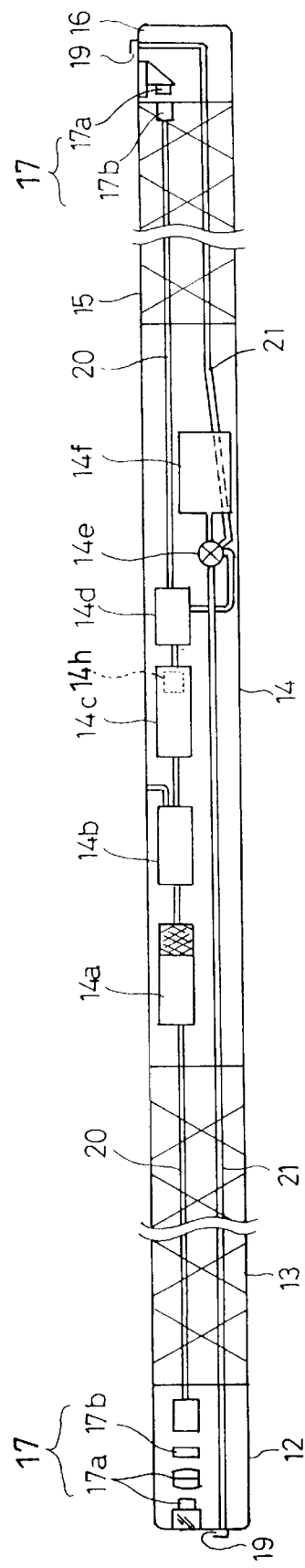
FIG. 2 is a schematic cross sectional view of the first embodiment of the rod-shaped endoscope body, according to the present invention.
Figure 3:
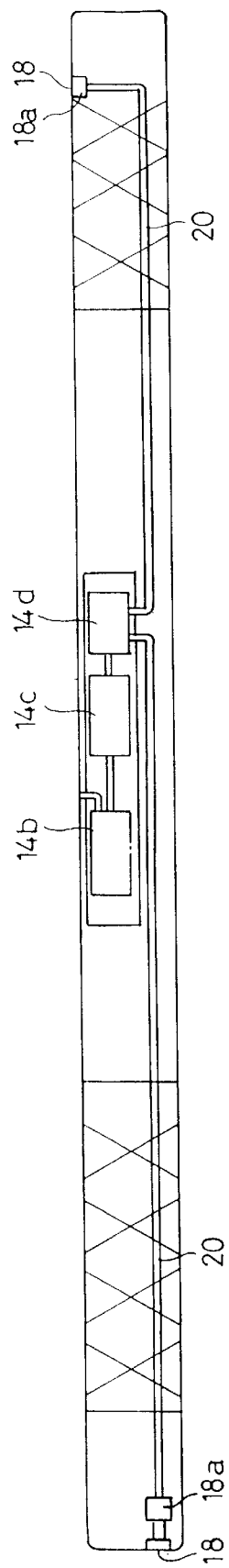
FIG. 3 is a schematic cross sectional view of the rod-shaped endoscope body shown in FIG. 2, taken along a different plane.

FIGS. 2 and 3 show the first embodiment of the rod-shaped endoscope body 10. The rod-shaped endoscope body 10 is provided with a first hard portion (unbendable portion) 12, a first bending portion 13, a flexible portion 14, a second bending portion 15 and a second hard portion (unbendable portion) 16, in this order from the front end (the left end as viewed in FIG. 2). The first bending portion 13 and the flexible portion 14 constitute a bendable portion, and the second bending portion 15 and the flexible portion 14 constitute another bendable portion. The rod-shaped endoscope body 10 is entirely covered by an elastic covering 29 whose outer surface is smooth and well-slidable (see FIG. 26). The first and second hard portions 12 and 16 are each made of a hard material (e.g., a hard plastic) which is not macroscopically deformable. The flexible portion 14 is designed to be bendable along the shape of a digestive tract when it is inserted in the body cavity.

Each of the first and second hard portions 12 and 16 is provided therein with an observing system 17, an illumination window 18 and an air supply port 19. The observing system 17 provided in the first hard portion 12 is a front-view observing system for viewing from the front of the first hard portion 12. However, the observing system 17 provided in the second hard portion 16 is a side-view observing system for viewing from the side of the second hard portion 16. Each observing system 17 includes an objective optical system 17a and a CCD image sensor 17b. The flexible portion 14 is provided therein with an amplifier circuit 14a, a transmitter/receiver device 14b, a power supplying device 14c, a control circuit 14d, a compressed air tank 14f and a microwave receiver 14h. Each CCD image sensor 17b is connected to the amplifier circuit 14a via a corresponding signal line 20. The amplifier circuit 14a is connected to the transmitter/receiver device 14b, which is positioned in the flexible portion 14. Each of the hard portions 12 and 16 is provided therein with an LED (light emitter) 18a which is secured to the corresponding illumination window 18. Each LED 18a is connected to the control circuit 14d via a corresponding signal line 20 (see FIG. 3).

Each air supply port 19 is connected to the outer end of a corresponding air supply tube 21. The inner end of each air supply tube 21 is connected to a valve 14e of the compressed air tank 14f. The valve 14e is controlled to open or shut by the control circuit 14d. The power supplying device 14c is connected to the transmitter/receiver device 14b and the control circuit 14d. The power supplying device 14c converts a microwave received by the microwave receiver 14h into electrical current to supply the same to the transmitter/receiver device 14b and the control circuit 14d. The microwave received by the microwave receiver 14h is transmitted from the external device 11.

Figure 26:
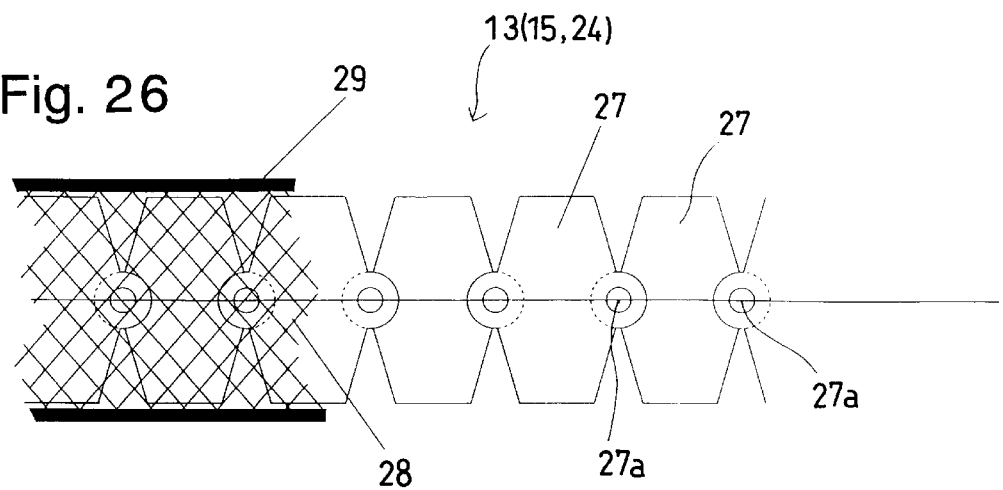
FIG. 26 is a schematic side view of part of the first embodiment of each bending portion, with parts omitted for clarity, in the case where the bending portion is designed to be bendable in a single plane.

FIG. 26 shows part of the first embodiment of each of the first and second bending portions 13 and 15 in the case where each bending portion is designed to be bendable in a single plane. The first embodiment of each bending portion is provided with an articulated series of ring joints 27. Adjacent ring joints 27 are connected with each other by a shaft 27a so that each of the adjacent ring joints 27 can rotate about the shaft 27a. All the shafts 27a are parallel to one another so as to lie in a common plane. The articulated series of ring joints 27 having such a structure is covered by a steel wired tube 28. This steel wired tube 28 is covered by the aforementioned elastic covering 29. Each of the first and second bending portions 13 and 15 is designed to be more flexible and bendable than the flexible portion 14 to bend from the flexible portion 14.

Figure 4:
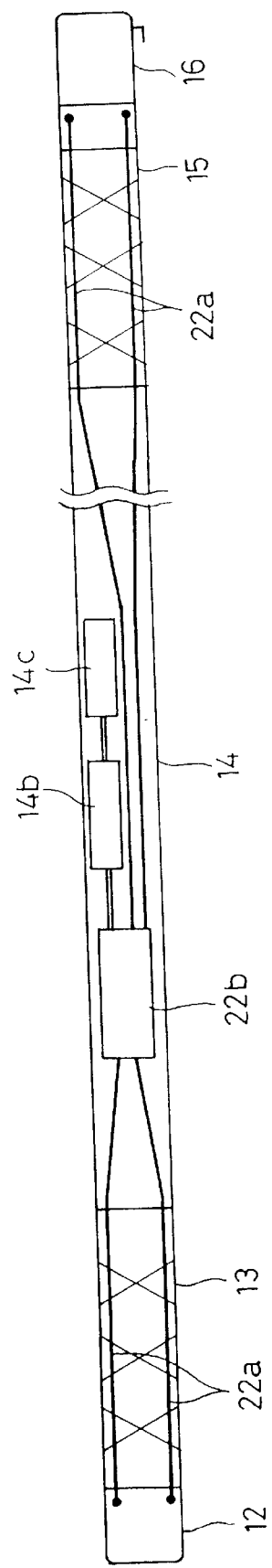
FIG. 4 is a schematic cross sectional view of the rod-shaped endoscope body shown in FIG. 2, showing a radio-controlled bending device thereof.

The rod-shaped endoscope body 10 is provided therein with a plurality of bendable drive wires (two wires in the first embodiment of the first bending portion 13) 22a which extend within the first bending portion 13 and the flexible portion 14 (see FIG. 4). Each drive wire 22a is made of a shape memory alloy (SMA) which bends when supplied with electrical current to be heated thereby. The rod-shaped endoscope body 10 is further provided therein with a selective-heating device 22b which is connected to the transmitter/receiver device 14b. The drive wires 22a, the selective heating device 23, and the transmitting/receiving device 14b constitute a radio-controlled driving device. The outer ends of the drive wires 22a are each secured to the first hard portion 12, while the inner ends of the drive wires 22a are each secured to the selective-heating device 22b.

The two drive wires 22a are diametrically arranged at opposite sides of the axis of the cylindrical first bending portion 13. The selective-heating device 22b is a circuit which selectively supplies electrical current to the two drive wires 22a to heat the same in accordance with control signals output from the transmitter/receiver device 14b, which makes it possible to bend the first bending portion 13 in a plane in which the two drive wires 22a lie.

Figure 25:
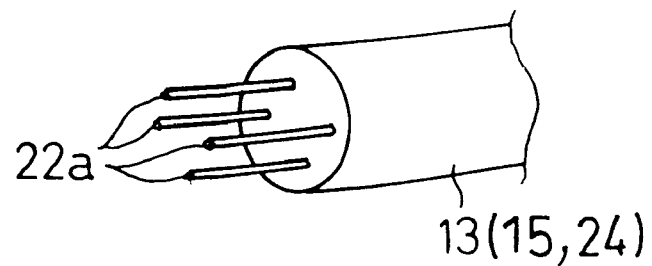
FIG. 25 is an explanatory view of part of a bending portion of the rod-shaped endoscope body, showing an arrangement of the bendable drive wires provided in the bending portion.
Figure 27:
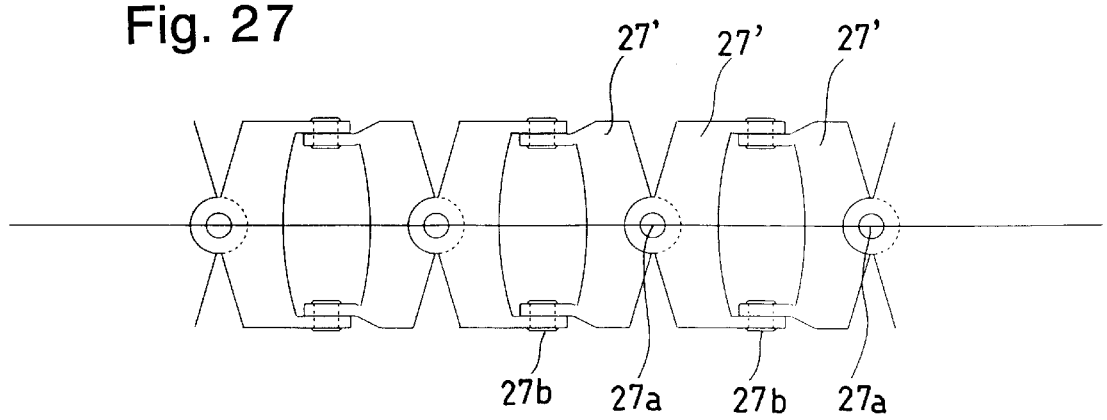
FIG. 27 is a schematic side view of part of the second embodiment of each bending portion, in the case where the bending portion is designed to be bendable in two planes perpendicular to each other.

When it is required that the first bending portion 13 be bendable only in a single plane, it is sufficient that the rod-shaped endoscope body 10 be provided with the first embodiment of the first bending portion 13, as shown in FIG. 26, which can bend only in a single plane. When it is required that the first bending portion 13 be bendable in two planes perpendicular to each other, the first bending portion 13 needs to have a structure such as shown in FIG. 27. FIG. 27 shows part of the second embodiment of each of the first and second bending portions 13 and 15 in the case where it is designed to be bendable in two planes perpendicular to each other. The second embodiment of each bending portion is provided with an articulated series of ring joints 27'. Adjacent ring joints 27' are connected with each other by a first shaft 27a or a second shaft 27b so that each of the adjacent ring joints 27' can rotate about each of the shafts 27a and 27b. The first and second shafts 27a and 27b extend in directions perpendicular to each other and are alternately arranged. In FIG. 27 neither the steel wired tube 28 nor the aforementioned elastic covering 29 is illustrated for clarity of illustration. In the second embodiment of the first bending portion 13, four bendable drive wires 22a extend within the first bending portion 13 and the flexible portion 14 (see FIG. 25). The outer ends of the four drive wires 22a are each secured to the first hard portion 12 at 90° intervals about the axis of the first hard portion 12. The inner ends of each pair of drive wires 22a which are diametrically opposite to each other are secured to the selective-heating device 22b. In the second embodiment of the first bending portion 13, although only two drive wires 22a are shown in FIG. 4, the remaining two drive wires 22a are provided in a similar manner.

The second bending portion 15 is controlled to bend similar to the first bending portion 13. Namely, the rod-shaped endoscope body 10 is provided therein with another plurality of bendable drive wires (two wires when the second bending portion 15 needs to be bendable only in a single plane, or four drive wires when the second bending portion 15 needs to be bendable in two planes perpendicular to each other) 22a for the second bending portion 15 (see FIG. 4). The structure of the mechanism for driving the first bending portion 13 using the drive wires 22a is substantially identical to that for driving the second bending portion 15 except that the tips of the drive wires 22a for manipulating the second bending portion 15 are each secured to the second hard portion 16, whereas the tips of the drive wires 22a for manipulating the first bending portion 13 are each secured to the first hard portion 12.

The external device 11 shown in FIG. 1 is provided with an external receiving portion 11a, a monitor 11b, a bending portion controller portion (operational portion) 11c, an external transmitting portion 11d, a valve controlling portion 11e and a microwave transmitting portion (microwave transmitter) 11f. The external device 11 transmits the aforementioned microwave, which is used as a power supply for the rod-shaped endoscope body 10, from the microwave transmitting portion 11f to the rod-shaped endoscope body 10. This transmitted microwave is received by the microwave receiver 14h and is converted into electrical current by the power supplying device 14c. The power supplying device 14c supplies the electrical current to the transmitter/receiver device 14b and the control circuit 14d. By manually operating the bending portion controller portion 11c and the valve controlling portion 11e of the external device 11, radio operational signals for operating the first or second bending portion 13 or 15 and the valve 14e are generated by the external device 11 to be transmitted to the rod-shaped endoscope body 10 via the external transmitting portion 11d. The external receiving portion 11a receives the image signals (radio waves) transmitted from the transmitter/receiver device 14b. The received image signals are displayed on the monitor 11b to be observed by an operator.

In the present embodiment of the fully-swallowable endoscopic system, the transmitter/receiver device 14b of the rod-shaped endoscope body 10 receives the radio operational signals transmitted from the external transmitting portion 11d of the external device 11 so that each of the fundamental operational elements of the rod-shaped endoscope body 10 can be radio-controlled by operating the external device 11. The power supplying device 14c supplies electrical current to the transmitter/receiver device 14b and the control circuit 14d by converting the received microwave into the electrical current, so that the operator does not have to care about the remaining battery power of the rod-shaped endoscope body 10. This makes it possible to observe the target inner part of the body sufficiently.

Figure 10:
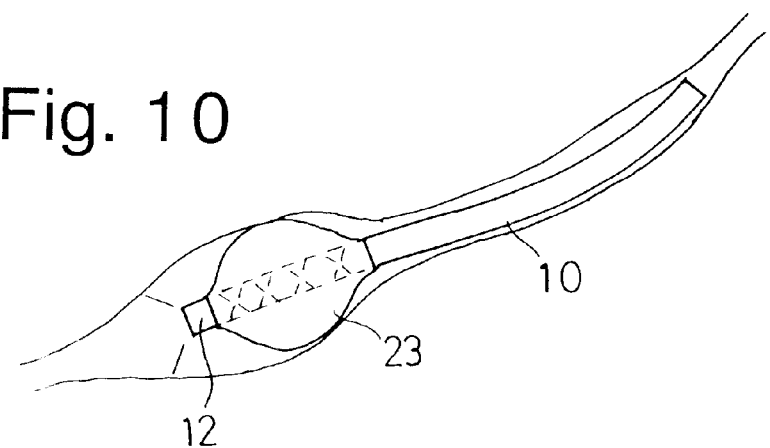
FIG. 10 is an explanatory view of the rod-shaped endoscope body shown in FIG. 9 which is positioned in an alimentary canal, showing a state where the endoscope is fixed to the inner wall of the alimentary canal by inflating a balloon provided at the front end of the endoscope.

Each LED 18a, which receives power from the power supplying device 14c via the corresponding signal line 20, emits light outwardly through the corresponding illumination window 18. The object image upon which the illumination light of each LED 18a is impinged is formed on the sensitive surface of the corresponding CCD image sensor 17b through the corresponding objective optical system 17a. The image signal supplied from each CCD image sensor 17b is amplified by the amplifier circuit 14a. This amplified image signal is transmitted from the transmitter/receiver device 14b to be subsequently received by the external receiving portion 11a of the external device 11. The image signal received by the external device 11 is observed on the monitor 11b (see FIG. 10). The operator operates the bending portion controller portion 11c of the external device 11 to bend the first bending portion 13 or the second bending portion 15 via the selective-heating device 22b, which is controlled by the radio operational signals transmitted from the external transmitting portion 11d, to thereby change the direction of the objective optical system 17a to observe the target inner part of the body. At this time, if a tubular passage in a body is made to inflate by sending the compressed air in compressed air tank 14f from the corresponding air supply port 19 to the tubular passage via the corresponding air supply tube 21 by operating the valve controlling portion 11e of the external device 11, so that the transmitter/receiver device 14b receives radio operational signals transmitted from the external transmitting portion 11d, so as to operate the valve 14e, the distance between the first or second hard portion 12 or 16 and the inner wall of the tubular passage becomes large, which makes it easy to observe the inner wall of the tubular passage.

Figure 5:
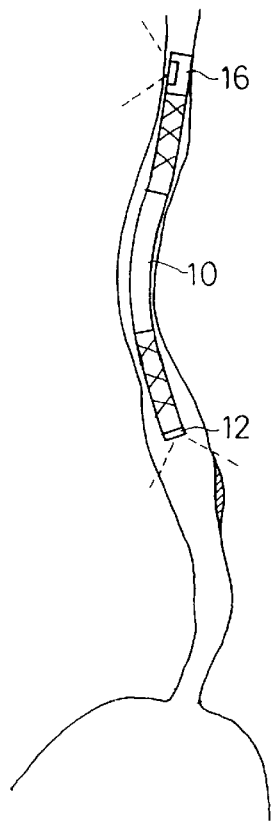
FIG. 5 is an explanatory view of the first embodiment of the rod-shaped endoscope body which is positioned in the esophagus, showing a state where the inside of the esophagus is observed with the endoscope.
Figure 6:
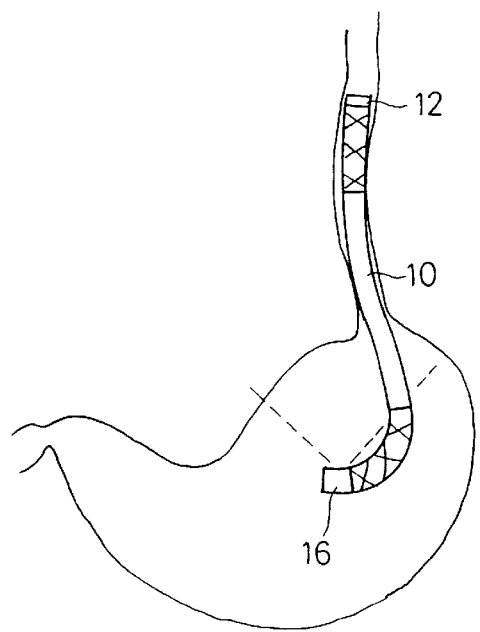
FIG. 6 is an explanatory view of the first embodiment of the rod-shaped endoscope body which is positioned between the esophagus and the stomach, showing a state where an inside upper part of the stomach is observed with the side viewing-type of observing system.
Figure 8:
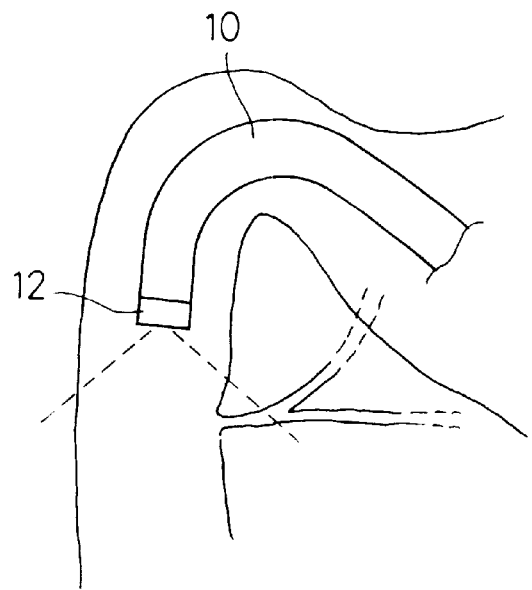
FIG. 8 is an explanatory view of part of the first embodiment of the rod-shaped endoscope body which is positioned between the stomach and the duodenum, showing a state where the papilla of Vater is observed with the front-view observing system.

In the endoscope constructed as above, a patient to be examined swallows the rod-shaped endoscope body 10 entirely. After being swallowed entirely, the rod-shaped endoscope body 10 is radio-controlled to proceed gradually in the alimentary canal by peristalsis. In the case where the inside of the alimentary canal such as the esophagus needs to be observed with the endoscope 10, it is more effective for the patient swallow the endoscope 10 from the first hard portion 12, as can be seen in FIG. 5. On the other hand, in the case where the inside of a large internal organ such as the stomach needs to be observed with the endoscope 10, it is more effective for the patient swallow the endoscope 10 from the second hard portion 16, as can be seen in FIG. 6. In the case of observing the papilla of Vater, if the patient swallows the endoscope 10 from the first hard portion 12, the papilla of Vater cannot be clearly observed using the observing system (front-view observing system) 17 provided in the first hard portion 12 as shown in FIG. 8. However, in the same case, if the patient swallows the endoscope 10 from the second hard portion 16, the papilla of Vater can be clearly and easily observed using the observing system (side-view observing system) 17 provided in the second hard portion 16.

Figure 9:
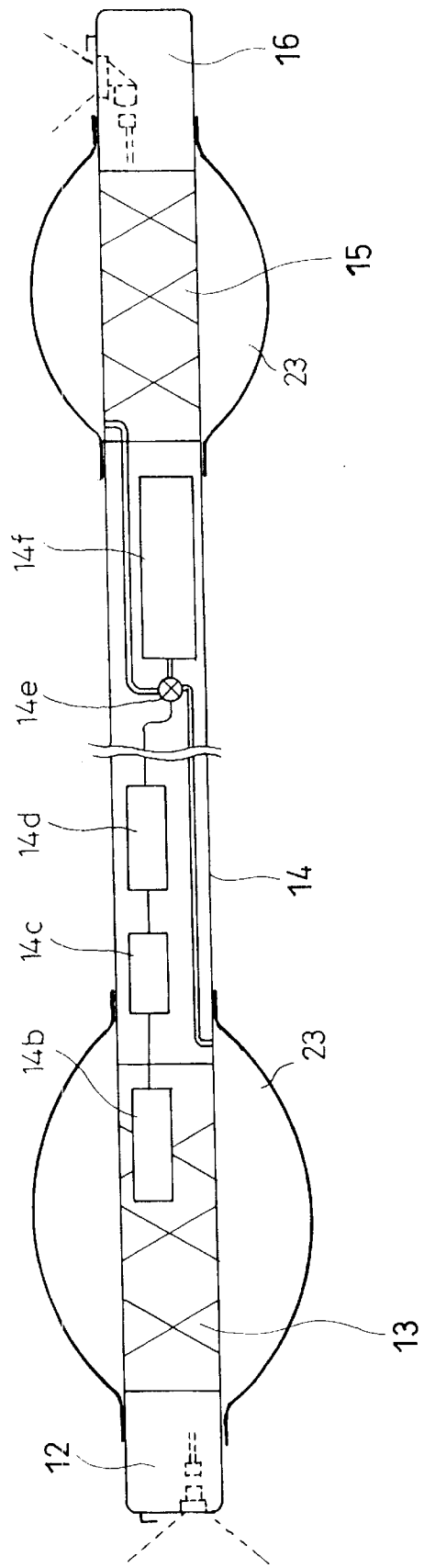
FIG. 9 is a schematic cross sectional view of the second embodiment of the rod-shaped endoscope body, according to the present invention.
Figure 11:
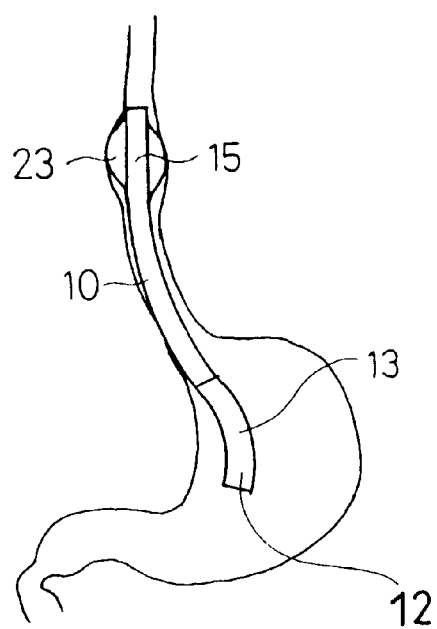
FIG. 11 is an explanatory view of the rod-shaped endoscope body shown in FIG. 9 which is positioned between the esophagus and the stomach, showing a state where the endoscope is fixed to the inside of the esophagus by inflating a balloon provided at the rear end of the endoscope.
Figure 12:
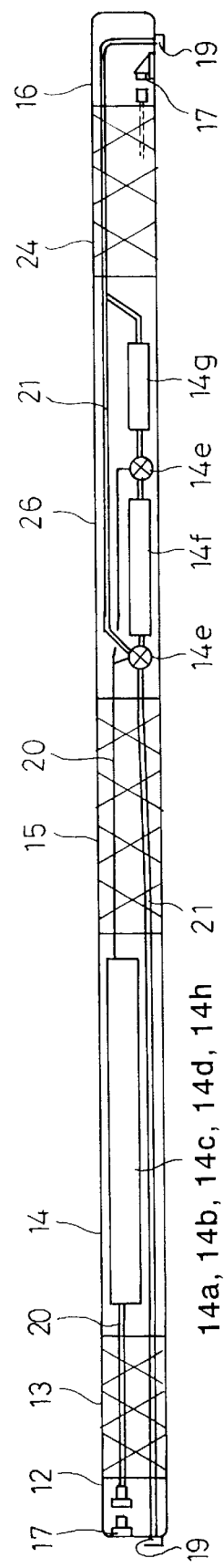
FIG. 12 is a schematic cross sectional view of the third embodiment of the rod-shaped endoscope body, according to the present invention.
Figure 13:
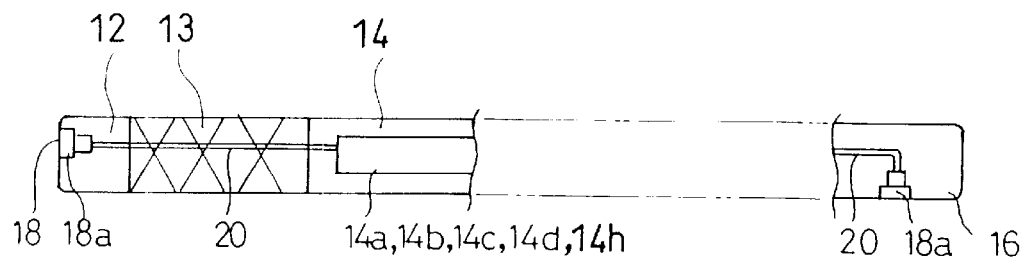
FIG. 13 is a schematic cross sectional view of the rod-shaped endoscope body shown in FIG. 12, taken along a different plane.

FIG. 9 shows the second embodiment of the rod-shaped endoscope body 10. This rod-shaped endoscope body 10 is provided with two balloons 23 respectively provided at the opposite ends of the rod-shaped endoscope body 10 as shown in FIG. 9. The endoscope 10 can be provided with only one balloon 23 at either end. The second embodiment of the endoscope 10 is substantially identical to the first embodiment of the endoscope 10 except that the second embodiment of the endoscope 10 is further provided with the balloons 23. Each balloon 23 can be inflated by sending the compressed air in the compressed air tank 14f into the balloon 23, by operating the valve controlling portion 11e of the external device 11, so that the transmitter/receiver device 14b receives the radio operational signals transmitted from the external transmitting portion 11d, so as to operate the valve 14e. For instance, in the case where the second embodiment of the rod-shaped endoscope 10 is in a tubular passage in a body, if the balloon 23 provided at the front end of the endoscope 10 is inflated, the distance between the hard portion 12 and the inner wall of the tubular passage becomes large, which makes it easy to observe the inner wall of the tubular passage (see FIG. 10). Conversely, if the balloon 23 provided at the rear end of the endoscope 10 is inflated, the endoscope 10 can be held stably at a desired position in a case as shown in FIG. 11, and the target inner part can be easily observed by manipulating the first bending portion 13.

FIGS. 12 through 17 show the third embodiment of the rod-shaped endoscope body 10. The rod-shaped endoscope body 10 is provided with a first hard portion (unbendable portion) 12, a first bending portion 13, a first flexible portion 14, a second bending portion 15, a second flexible portion 26, a third bending portion 24 and a second hard portion (unbendable portion) 16, in this order from the front end (the left end as viewed in FIG. 12). The first and second flexible portions 14 and 16, and respective neighboring first, second, and third bending portions 13, 15 and 24 connected thereof, each constitute a bendable portion. The rod-shaped endoscope body 10 is entirely covered by an elastic covering 29 whose outer surface is smooth and well-slidable (see FIG. 26). The first and second hard portions 12 and 16 are each made of a hard material (e.g., a hard plastic) which is not macroscopically deformable. Each of the first and second flexible portions 14 and 26 is designed to be bendable along the shape of a digestive tract when it is inserted in the body cavity.

Each of the hard portions 12 and 16 is provided therein with an observing system 17, an illumination window 18 and an air supply port 19. Each observing system 17 includes an objective optical system 17a and a CCD image sensor 17b. The first flexible portion 14 is provided therein with an amplifier circuit 14a, a transmitter/receiver device 14b, a power supplying device 14c, a control circuit 14d and a microwave receiver 14h. Each CCD image sensor 17b is connected to the amplifier circuit 14a via a corresponding signal line 20. The amplifier circuit 14a is connected to the transmitter/receiver device 14b, which is positioned in the first flexible portion 14. Each of the hard portions 12 and 16 is provided therein with an LED (light emitter) 18a secured to the corresponding illumination window 18. Each LED 18a is connected to the control circuit 14d via a corresponding signal line 20 (see FIG. 13).

The second flexible portion 26 is provided therein with a compressed air tank 14f and a water tank 14g which are each provided with a corresponding valve 14e. Each air supply port 19 is connected to the outer end of a corresponding air supply tube 21. The inner end of each air supply tube 21 is connected to the corresponding valve 14e. Each valve 14e is controlled to open or shut by the control circuit 14d. The power supplying device 14c is connected to the transmitter/receiver device 14b and the control circuit 14d. The power supplying device 14c converts a microwave received by the microwave receiver 14h into electrical current to supply the same to the transmitter/receiver device 14b and the control circuit 14d. The microwave received by the microwave receiver 14h is transmitted from the external device 11.

FIG. 26 also shows part of the first embodiment of each of the first, second and third bending portions 13, 15 and 24 in the case where each bending portion is designed to be bendable in a single plane. The first embodiment of each bending portion is provided with an articulated series of ring joints 27. Adjacent ring joints 27 are connected with each other by a shaft 27a so that each of the adjacent ring joints 27 can rotate about the shaft 27a. All the shafts 27a are parallel to one another so as to lie in a common plane. The articulated series of ring joints 27 having such a structure is covered by a steel wired tube 28. This steel wired tube 28 is covered by the aforementioned elastic covering 29. Each of the first, second and third bending portions 13, 15 and 24 is designed to be more flexible and bendable than the first and second flexible portions 14 and 26.

Each of the second and third bending portions 15 and 24 is controlled to bend similar to the first bending portion 13. Namely, the rod-shaped endoscope body 10 is provided therein with another plurality of bendable drive wires (two drive wires when the bending portion needs to be bendable only in a single plane, or four drive wires when the bending portion needs to be bendable in two planes perpendicular to each other) 22a for each of the second and third bending portions 15 and 24 (see FIG. 14). The structure of the mechanism for driving the first bending portion 13 using the drive wires 22a is substantially identical to that for driving each of the second and third bending portions 15 and 24 except that the tips of the drive wires 22a for manipulating the second bending portion 15 are each secured to the second flexible portion 26 while the tips of the drive wires 22a for manipulating the third bending portion 24 are each secured to the second hard portion 16, whereas the tips of the drive wires 22a for manipulating the first bending portion 13 are each secured to the first hard portion 12.

Figure 16:
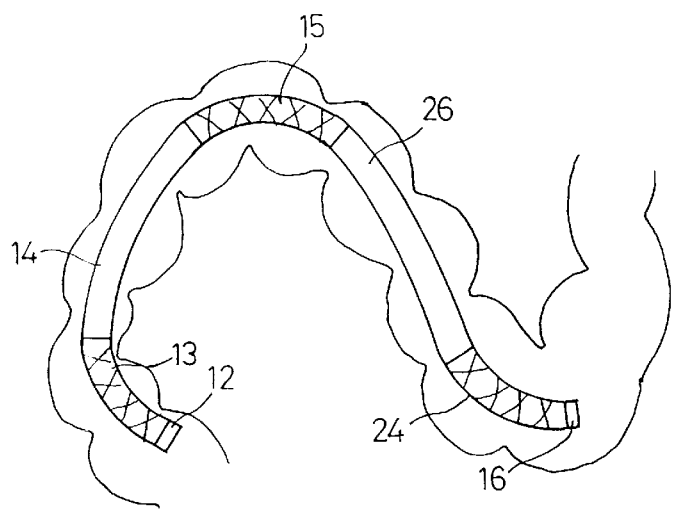
FIG. 16 is an explanatory view of the rod-shaped endoscope body shown in FIG. 12, showing a state where the endoscope is introduced in the large intestine.
Figure 17:
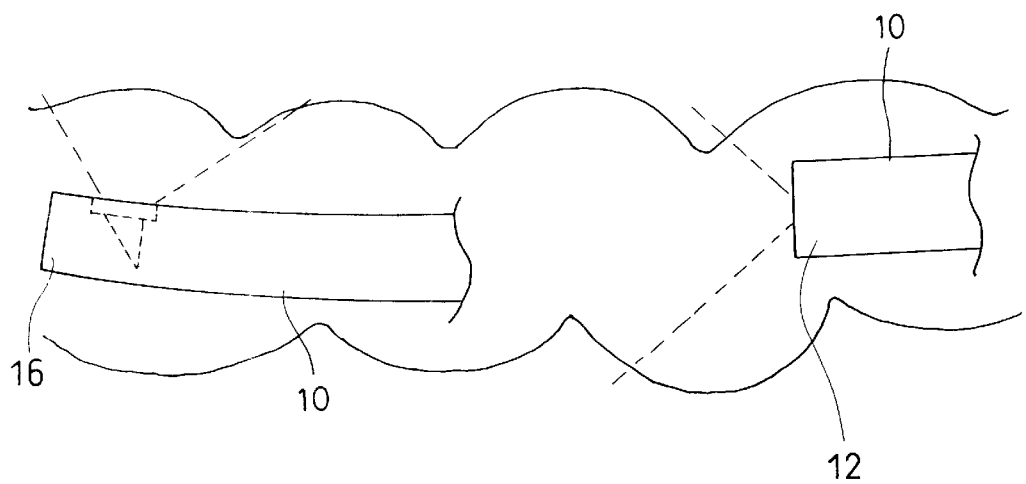
FIG. 17 is an explanatory view of part of the rod-shaped endoscope body shown in FIG. 12, showing a state where the inside of a tubular passage in a body is observed with the front-view observing system and the side-view observing system of the endoscope.

According to the third embodiment of the rod-shaped endoscope body 10, since the endoscope 10 is provided between the first and second flexible portions 14 and 26 with the second bending portion 15, which is designed to be more flexible and bendable than the first and second flexible portions 14 and 26, the rod-shaped endoscope 10 can be easily introduced in a tubular passage of an internal organ such as the large intestine (see FIG. 16). Furthermore, as shown in FIG. 17, the side-view observing system provided in the second hard portion 16 can compensate for the blind spots of the front-view observing system provided in the first hard portion 12, which makes it possible to observe the target inner part of the body reliably and precisely.

Figure 20:
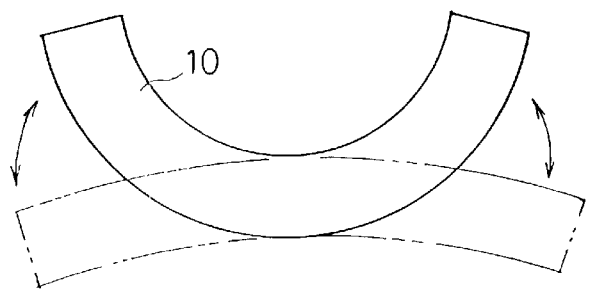
FIG. 20 is a schematic cross sectional view of the rod-shaped endoscope body shown in FIG. 18, showing a state where the endoscope bends.
Figure 18:
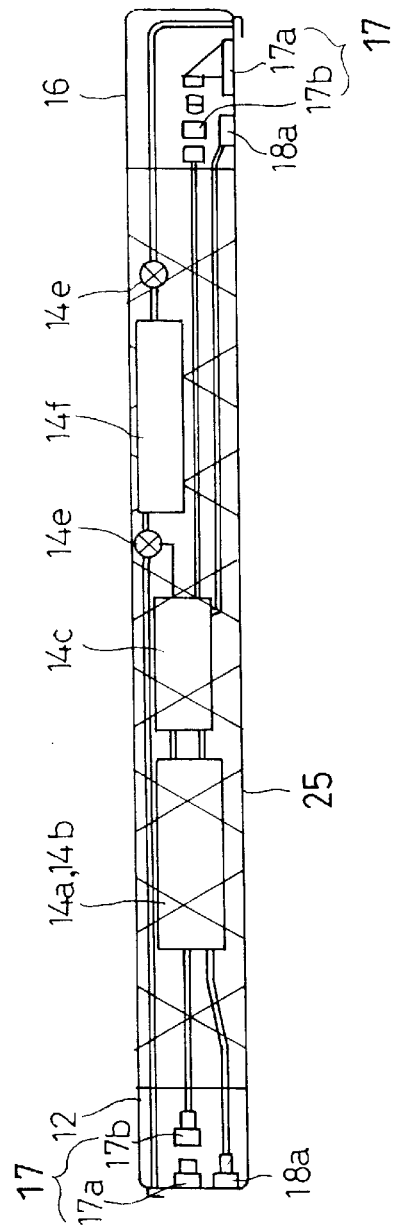
FIG. 18 is a schematic cross sectional view of the fourth embodiment of the rod-shaped endoscope body, according to the present invention.
Figure 19:
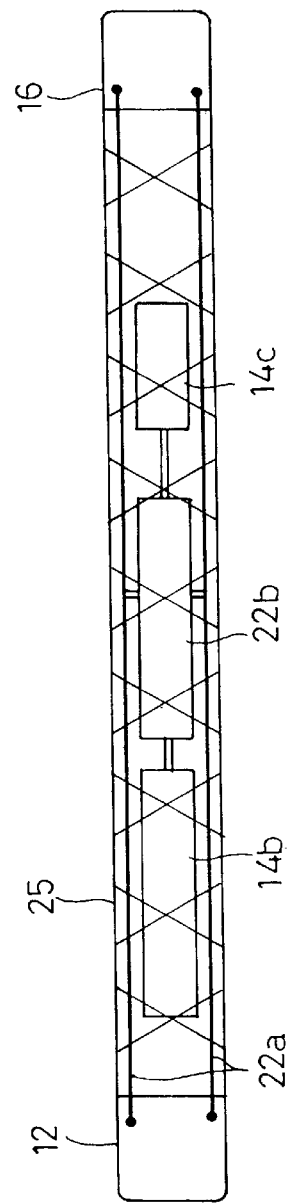
FIG. 19 is a schematic cross sectional view of the rod-shaped endoscope body shown in FIG. 18, showing a radio-controlled bending device thereof.

FIGS. 18 through 20 show the fourth embodiment of the rod-shaped endoscope body 10. This endoscope 10 is provided with a first hard portion 12, a bendable portion 25 and a second hard portion 16, in this order from the front end (the left end as viewed in FIG. 18). The first and second hard portions 12 and 16 are each made of a hard material (e.g., a hard plastic) which is not macroscopically deformable. The outer periphery of the bendable portion 25 is made of a bendable and flexible tube such as a steel wired tube so that the entire bendable portion 25 can bend. The first hard portion 12 is provided therein with an observing system (front-view observing system) 17, and the second hard portion 16 is provided therein with an observing system (side-view observing system) 17. Similar to the first embodiment of the rod-shaped endoscope body 10, the rod-shaped endoscope body 10 can be provided therein with a plurality of bendable drive wires (two drive wires when the bendable portion 25 needs to be bendable only in a single plane, or four drive wires when the bendable portion 25 needs to be bendable in two planes perpendicular to each other) 22a, so as to manipulate the endoscope 10 to bend in a manner such as shown in FIG. 20.

Figure 7:
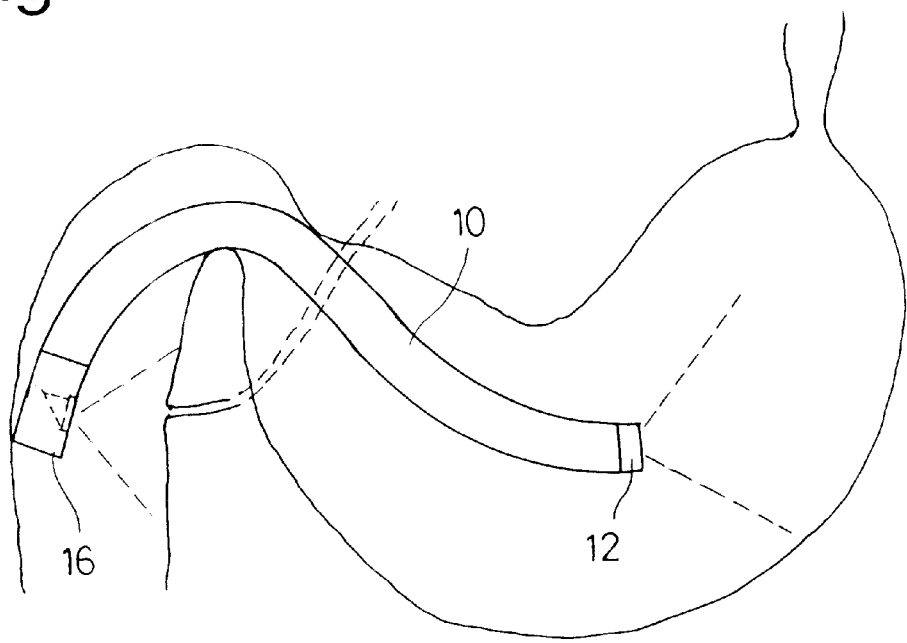
FIG. 7 is an explanatory view of the first embodiment of the rod-shaped endoscope body which is positioned between the stomach and the duodenum, showing a state where the papilla of Vater is observed with the side-view observing system.
Figure 24:
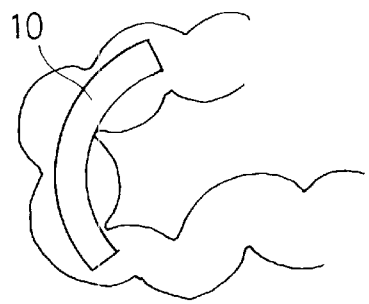
FIG. 24 is an explanatory view of the rod-shaped endoscope body shown in FIG. 19 or 21, showing a state where the endoscope is introduced in a curved tubular passage in a body.
Figure 14:
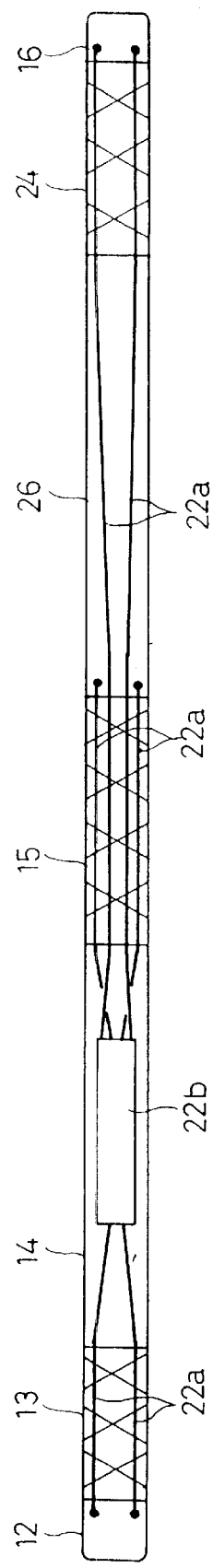
FIG. 14 is a schematic cross sectional view of the rod-shaped endoscope body shown in FIG. 12, showing a radio-controlled bending device thereof.
Figure 15:
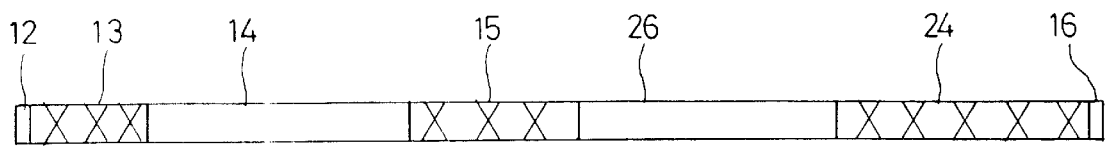
FIG. 15 is a schematic side view of the rod-shaped endoscope body shown in FIG. 12.
Figure 21:
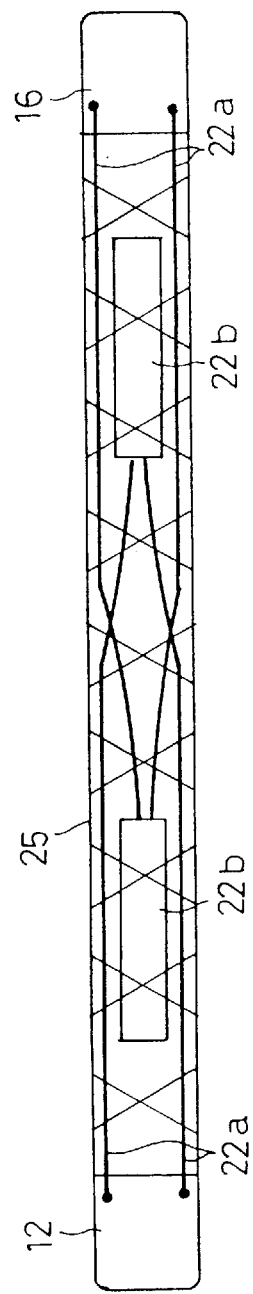
FIG. 21 is a schematic cross sectional view of the fifth embodiment of the rod-shaped endoscope body, according to the present invention.
Figure 22:
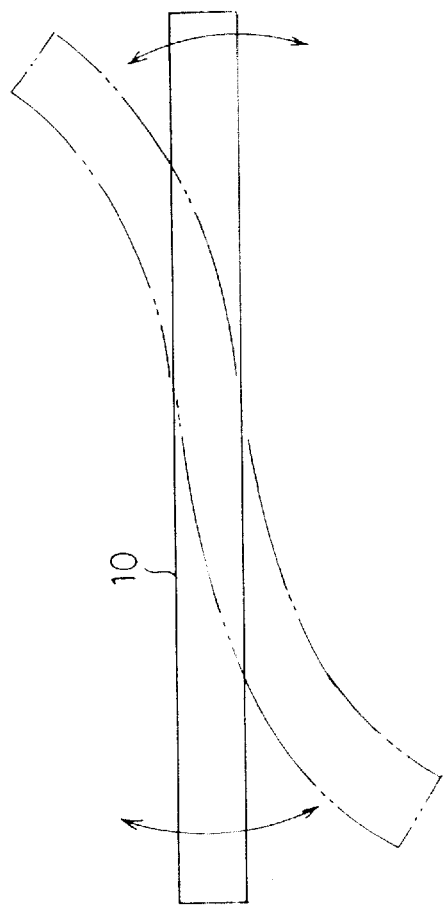
FIG. 22 is a schematic cross sectional view of the rod-shaped endoscope body shown in FIG. 21, showing a state where the endoscope bends.
Figure 23:
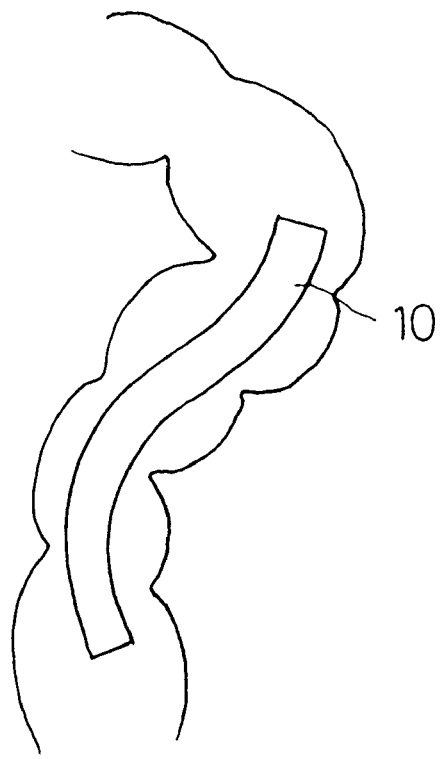
FIG. 23 is an explanatory view of the rod-shaped endoscope body shown in FIG. 21, showing a state where the endoscope is introduced in a curved tubular passage in a body.

FIGS. 21 and 22 show the fifth embodiment of the rod-shaped endoscope body 10. The fifth embodiment of the endoscope 10 is substantially identical to the fourth embodiment of the endoscope 10 except that the fifth embodiment of the endoscope 10 is provided with a first plurality of drive wires 22a for manipulating the front half of the endoscope 10 (the left half as viewed in FIG. 21), a second plurality of drive wires 22a for manipulating the rear half of the endoscope 10 (the right half as viewed in FIG. 21), and two selective-heating devices 22b. The outer and inner ends of the first plurality of the drive wires 22a are each secured to the first hard portion 12 and the first selective-heating device 22b (the right selective-heating devices 22b as viewed in FIG. 21), respectively, while the outer and inner ends of the second plurality of the drive wires 22a are each secured to the second hard portion 16 and the second selective-heating device 22b (the left selective-heating devices 22b as viewed in FIG. 21), respectively. According to this structure, the front half of the endoscope 10 can be manipulated to bend independently of the rear half of the endoscope 10, and vice versa. Accordingly, the front half and the rear half of the endoscope 10 can be manipulated to bend in the same direction as shown in FIG. 20, or in the opposite directions as shown in FIG. 22. This makes it easier to introduce the endoscope 10 in a complicatedly curved tubular passage in a body (see FIGS. 7 and 8) and makes it possible to observe the target inner part of the body thoroughly (see FIGS. 23 and 24).

The power supplying device 14c of the rod-shaped endoscope body 10 can be replaced by a built-in battery to simplify the structure of endoscopic system.

As can be understood from the foregoing, according to the fully-swallowable endoscopic system to which the present invention is applied, since the rod-shaped endoscope body is entirely positioned in a body cavity without any cables or wires which connect the rod-shaped endoscope body with the external device, a patient to be examined does not suffer from pain even if the endoscope is retained in the patient's body for a long time. Furthermore, since a target inner part of the body can be viewed from more than one direction, the target inner part of the body can be observed reliably and precisely with few blind spots.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscopic system comprising:
a rod-shaped endoscope body which can be entirely swallowed by a patient to be examined so as to be located in a body cavity, said rod-shaped endoscope body including at least one bendable portion which is bendable along a curve of said body cavity; and
an external device provided separately from said rod-shaped endoscope body without a mechanical connection with said rod-shaped endoscope body;
said rod-shaped endoscope body comprising:
at least two light emitters;
at least two observing systems;
a transmitter that transmits a radio wave which carries an image formed by said observing systems; and
a power supplying device,
said external device comprising a receiver that receives said radio wave which carries said image,
said bendable portion comprising a bending portion that is configured to be bent by radio control from the external device so as to orient at least one of said two light emitters and at least one of said two observing systems in a predetermined direction, and a flexible portion that is configured to be bent by an external force along a curve of the body cavity, said bending portion being configured to be more flexible than said flexible portion.

2. The endoscopic system according to claim 1, wherein one of said at least two light emitters and one of said at least two observing systems are provided in one of the opposite ends of said rod-shaped endoscope body, and wherein another one of said at least two light emitters and another one of said at least two observing systems are positioned in the other of said opposite ends of said rod-shaped endoscope body.

3. The endoscopic system according to claim 2, wherein each of said one and said another of said at least two observing systems is a front-view observing system for viewing from the front of a corresponding one of said opposite ends of said rod-shaped endoscope body.

4. The endoscopic system according to claim 2, wherein said one of said at least two observing systems is a front-view observing system for viewing from the front of a corresponding one of said opposite ends of said-rod-shaped endoscope body; and wherein said another one of said at least two observing systems if a side-view observing system for viewing from the side of said rod-shaped endoscope body.

5. The endoscopic system according to claim 1, wherein said rod-shaped endoscope body is provided with a radio-controlled driving device which receives a radio operational signal transmitted from said external device to bend said bending portion in accordance with said radio operational signal; and wherein said external device comprises an operational portion which is operated to transmit said radio operational signal to said radio-controlled driving device.

6. The endoscopic system according to claim 1, wherein said at least one bendable portion comprises a plurality of bendable portions arranged at different positions in the longitudinal direction of said rod-shaped endoscope body.

7. The endoscopic system according to claim 5, wherein said radio-controlled driving device comprises a plurality of drive wires made of a shape memory alloy, and a selective-heating device which selectively heats said plurality of drive wires to bend said bending portion.

8. The endoscopic system according to claim 1, wherein said power supplying device comprises a built-in battery.

9. The endoscopic system according to claim 1, wherein said external device comprises a microwave transmitter for transmitting a microwave to said rod-shaped endoscope body; and wherein said power supplying device converts said microwave into electrical current to supply said electrical current to said rod-shaped endoscope body.

10. The endoscopic system according to claim 1, wherein each of said at least two observing systems comprises an objective optical system and a CCD image sensor.

11. The endoscopic system according to claim 1, wherein said external device comprises a monitor which visually indicates said image.

12. The endoscope system according to claim 1, said bending portion comprising a plurality of adjacently positioned articulated joints.

13. The endoscope system according to claim 1, said flexible portion being bendable along a curve of the body cavity independently of said external device.

14. An endoscopic system comprising:
a rod-shaped endoscope body comprising at least one bending portion, at least one flexible portion connected to said at least one bending portion; at least two light emitters corresponding to at least two image pick-up devices, each image pick-up device taking an image of a target inner part illuminated by a corresponding one of said at least two light emitters; and a transmitter that transmits a radio wave which carries said image taken by each of said at least two image pick-up devices; and
a radio controller that controls said at least one bending portion to bend by radio-control, said bending portion being configured to be bent by radio control from the radio controller so as to orient at least one of said two light emitters and at least one of said two observing systems in a predetermined direction, said flexible portion being configured to be bent by an external force along a curve of the body cavity, said bending portion being configured to be more flexible than said flexible portion.

15. The endoscopic system according to claim 14, wherein said rod-shaped endoscope body further comprises a first hard portion fixed to one of the opposite ends of said rod-shaped endoscope body, and wherein said one of said at least two light emitters and one of said at least two image pick-up devices are fixed to said first hard portion.

16. The endoscopic system according to claim 15, wherein said rod-shaped endoscope body further comprises a second hard portion fixed to the other of said opposite ends of said rod-shaped endoscope body, and wherein said another one of said at least two light emitters and another one of said at least two image pick-up devices are fixed to said second hard portion.

17. The endoscopic system according to claim 14, wherein said radio controller comprises a monitor and a receiver for receiving said radio wave to indicate said image on said monitor.

18. The endoscopic system according to claim 14, wherein said radio controller further comprises a second transmitter for transmitting a microwave to said rod-shaped endoscope body, and wherein said rod-shaped endoscope body is provided therein with a power supplying device which receives said microwave to convert said microwave into electrical current which is to be used as a power source of said rod-shaped endoscope body.

19. The endoscope system according to claim 14, said bending portion comprising a plurality of adjacently positioned articulated joints.

20. The endoscope system according to claim 14, said flexible portion being bendable along a curve of the body cavity independently of said external device.

21. An endoscopic system comprising:

a rod-shaped endoscope body which can be swallowed by a patient to be examined so as to be in a body cavity, said rod-shaped endoscope body including at least one bendable portion which is bendable along a curve of said body cavity; and an external device provided separately from said rod-shaped endoscope body and without a mechanical connection to said rod-shaped endoscope body;

said rod-shaped endoscope body comprising at least two light emitters, at least two observing systems, a transmitter that transmits a radio wave which carries an image formed by said at least two observing systems and a power supply device;

said external device comprising a receiver that receives said radio wave which carries said image;

one of said at least two light emitters and one of said at least two observing systems being provided in one of the opposite ends of said rod-shaped endoscope body, and another one of said at least two light emitters and another one of said at least two observing systems being positioned in the other of said opposite ends of said rod-shaped endoscope body, one of said at least two observing systems comprising a front-view observing system that observes from a front of a corresponding end of said rod-shaped endoscope body, and another of said at least two observing systems comprising a side-view observing system that observes from a side of said rod-shaped endoscope body.

22. An endoscopic system comprising:

a rod-shaped endoscope body which can be swallowed by a patient to be examined so as to be in a body cavity, said rod-shaped endoscope body including at least one bendable portion which is bendable along a curve of said body cavity; and an external device provided separately from said rod-shaped endoscope body and without a mechanical connection to said rod-shaped endoscope body;

said rod-shaped endoscope body comprising at least two light emitters, at least two observing systems, a transmitter that transmits a radio wave which carries an image formed by said at least two observing systems and a power supply device;

said external device comprising a receiver that receives said radio wave which carries said image;

one of said at least two observing systems comprising a front-view observing system that observes from a front of an end of said rod-shaped endoscope body, and another of said at least two observing systems comprising a side-view observing system that observes from a side of said rod-shaped endoscope body.

* * * * *